United States Patent [19]
Kang et al.

[11] Patent Number: 6,106,815
[45] Date of Patent: Aug. 22, 2000

[54] SHAMPOO COMPOSITION CONTAINING METHYL VINYL ETHER/MALEIC ANHYDRIDE DECADIENE CROSSPOLYMER AND CAPSULES

[75] Inventors: Gil Sung Kang; In Ho Kim; Duk Bae Park, all of Inchun; Dong Tak Lee; Hae Hoon Park, both of Seoul, all of Rep. of Korea

[73] Assignee: Cheil Jedang Corporation, Seoul, Rep. of Korea

[21] Appl. No.: 09/091,887

[22] PCT Filed: Dec. 23, 1996

[86] PCT No.: PCT/KR96/00244

§ 371 Date: Dec. 18, 1998

§ 102(e) Date: Dec. 18, 1998

[87] PCT Pub. No.: WO97/23194

PCT Pub. Date: Jul. 3, 1997

[30] Foreign Application Priority Data

Dec. 26, 1995 [KR] Rep. of Korea ............... 95-56605

[51] Int. Cl.[7] .................. A61K 7/045; A61K 7/06; A61K 7/075; A61K 9/66
[52] U.S. Cl. ............ 424/70.12; 424/70.1; 424/70.11; 424/70.21; 424/70.22; 424/70.19; 424/451; 424/455; 424/489; 510/119; 514/881
[58] Field of Search ................... 424/70.1, 451, 424/455, 489, 70.11, 70.12, 70.21, 70.22, 70.19; 514/881; 510/119

[56] References Cited

U.S. PATENT DOCUMENTS

| | | |
|---|---|---|
| 4,126,674 | 11/1978 | Mausner . |
| 5,089,269 | 2/1992 | Noda et al. . |
| 5,275,761 | 1/1994 | Bergmann . |
| 5,391,368 | 2/1995 | Gerstein et al. . |
| 5,417,965 | 5/1995 | Janchitraponej et al. . |
| 5,587,174 | 12/1996 | Lang et al. . |
| 5,885,561 | 3/1999 | Flemming et al. . |
| 5,922,312 | 7/1999 | Jones et al. . |
| 5,961,994 | 10/1999 | Cauwet et al. . |
| 5,972,356 | 10/1999 | Peffly et al. . |

FOREIGN PATENT DOCUMENTS

| | | |
|---|---|---|
| 0 468 721 A1 | 1/1992 | European Pat. Off. . |
| 0 590 538 A1 | 4/1994 | European Pat. Off. . |

*Primary Examiner*—Thurman K. Page
*Assistant Examiner*—Brian K. Seidleck
*Attorney, Agent, or Firm*—Burns, Doane, Swecker & Mathis, L.L.P.

[57] ABSTRACT

A shampoo composition containing from 0.05% to 10% by weight of capsules or particles of 0.2 to 6.0 mm in diameter which include oily substances. The composition also includes from 5% to 65% by weight of surfactants, from 0.15% to 2% by weight of copolymer of methyl vinyl ether/maleic anhydride decadiene crosspolymer and from 0.1% to 2.0% by weight of polymeric conditioners. The presence of the crosspolymer significantly enhances the dispersion and stability properties of the capsules.

24 Claims, No Drawings

6,106,815

SHAMPOO COMPOSITION CONTAINING METHYL VINYL ETHER/MALEIC ANHYDRIDE DECADIENE CROSSPOLYMER AND CAPSULES

This application is a 371 of PCT/KR96/00244, filed Dec. 23, 1996.

BACKGROUND OF THE INVENTION

1. Field of the Invention

The present invention relates to a shampoo composition containing encapsulated or particulated oily substances. Particularly, the shampoo composition of the present invention ensures the homogeneous dispersion and stability of such capsules or particles for long periods and provides excellent conditioning and esthetic effects for the hair.

2. Description of the Prior Art

There are a variety of oily substances known as hair conditioning and esthetic agents, including mineral, animal and plant oils. However, due to their physicochemical properties, such oily substances are inconvenient for general use and application. Once such substances are incorporated into a shampoo, they are not readily applicable to the shampoo system and thus adversely effect the intrinsic performance of the shampoo, rather imparting the desired physical and esthetic properties to the hair.

To solve such problems, encapsulation has been developed in the art. Many prior patents have disclosed methods for producing microcapsules including water insoluble substances therein and hair care compositions containing the microcapsules. For example, Japanese Examined Patent Publication No. (Sho)46-38244 discloses a method of treating a capsule wall membrane such as gelatin with a cross-linking agent such as formaldehyde and glutaraldehyde, followed by drying and heating at a temperature of 120° C. to 150° C. Japanese Unexamined Patent Publication No. (Sho)56-100630 discloses a method of treating an aqueous dispersion containing a capsule having a wall membrane of polyvinyl alcohol with, for example, acids and dialdehydes such as glyoxal and glutaraldehyde; or acids and urea and/or melanine and formaldehyde; or alkali and divinylsulfone and/or methylvinyl ketone; or alkali and epichlorohydrin. Japanese Unexamined Patent Publication No. (Sho)56-100631 discloses a method of treating an aqueous dispersion containing a capsule having a wall membrane of polyvinyl alcohol with an organic titanium compound such as diisopropoxy titanium bisacetyl acetone and aminoalcohol titanium chelate. EP Publication No. 0590538 A1 discloses a transparent leave-on hair treatment composition including capsules of a water insoluble hair-treating compound encased in a shell material such as gelatin or acacia gum. U.S. Pat. No. 5,185,155 discloses a process for producing capsules containing a hydrophobic material with the use of silica particles whose size are all not greater than 100 nm. U.S. Pat. No. 4,115,315 discloses a process for producing capsules having pearlescent properties by the incorporation of pearlescent particles in the capsule walls thereof. U.S. Pat. No. 3,607,775 discloses minute capsules having walls which comprise a complex of at least two polymeric materials originally having opposite net electrical charges, with at least one of these polymeric materials being autogenously polymerizable to a solid polymeric material insoluble in the manufacturing vehicle. EP Publication No. 0332175 A2 discloses a method of producing a microcapsule capable of protecting a core substance by completly blocking a permeation of foreign materials, and having a high safety factor with respect to the human body.

As described above, most prior techniques for encapsulation do not cover aspects for keeping capsules homogenously and stably dispersed in the shampoo compositions.

For shampoo compositions containing encapsulated oily substances produced according to the aforementioned prior techniques, our experiments revealed that capsules in the diameter of about 0.3 mm or more floated on the upper phase of the shampoo system or precipitated to the bottom of the shampoo system. Moreover, some of capsules ruptured which lead to the release of oily substances into the shampoo system, which resulted in a considerable reduction of conditioning and esthetic properties.

There are few exemplary patents relating to techniques for the dispersion of particles having diameters of approximately 10 $\mu$m or less, for examples, U.S. Pat. Nos. 4,854,333 or 4,345,080, EP Publication Nos. 0285388, 0312234 or 0422508, and UK Patent No. 2187197. However, upon our examination of shampoo compositions produced as disclosed in such patents, we found that capsules containing oily substances were unsatisfactorily dispersed in the shampoo systems. Specifically, using the patented techniques, it was impossible to stably disperse capsules containing oily substances, with the specific gravity of the capsules being 0.5–0.95 at 25° C., into the shampoo systems.

Accordingly, the object of the present invention is to solve the above described problems and to provide an improved shampoo composition in which capsules containing oily substances are stably dispersed for a long period. The inventors developed a new shampoo system which ensures satisfactorily endured dispersion and stability of capsules containing oily substances therein.

SUMMARY OF THE INVENTION

The present invention relates to a shampoo composition containing capsulated or particulated oily substances, characterized by containing PVM/MA Decadiene Crosspolymer in amount from 0.15% to 2.0% by weight of the composition as a dispersing agent. The present shampoo compositions provide excellent conditioning and esthetic properties for hair in that the capsules or particles containing oily substances are stably dispersed therein. Since the present shampoo compositions ensure the stable dispersion of the capsules or particles for a long period, it is also advantageous in terms of storage. Additionally, since the present shampoo compositions retain a viscosity ranging from 4,000 cps to 20,000 cps at 25° C., it can be used conveniently.

DETAILED DESCRIPTION OF THE INVENTION

In the preferred embodiment, the present invention provides a shampoo composition which includes the following by weight of the compositon:

(a) from 0.05% to 10.0% of capsules or particles containing oily substances;

(b) from 5% to 65% of surfactants selected from anionic and amphoteric surfactants and mixtures thereof;

(c) from 0.15% to 2% of PVM/MA decadiene crosspolymer;

(d) from 0.5% to 10.0% of alkanolamides of fatty acids;

(e) from 0.1% to 2.0% of polymeric conditioners;

(f) from 0.1% to 4.0% of salts of alkylmethylammonium; and (g) from 0.15% to 2.0% of non-volatile silicones or fatty alcohols.

The capsules or particles according to the present invention has a diameter from 0.2 mm to 6.0 mm. Preferably, the diameter of the capsules or particles ranges from 0.3 mm to 3.0 mm. The thickness of the capsule walls is optional as far as the capsules are not ruptured in the system, but preferably ranges from 50 μm to 1,500 μm. The more preferable thickness is from 100 μm to 700 μm. The material of the capsule walls may be selected among a group consisting of agar, alginate, gelatin, polyamide, lactose, cellulose and derivatives thereof, and mixtures thereof. The possible amount of the capsules or particles ranges from 0.05% to 10.0% by weight of the shampoo composition, preferably from 0.15% to 6.0%.

The oily substances contained in capsules or as particles include mineral oils (e.g., liquid paraffin), lipid-soluble vitamin (e.g., vitamin E, vitamin A and derivatives thereof), ester oils (e.g., jojoba oil), some plant essential or cushion oils (e.g., meadowfoam oil and camellia oil) and animal oils (e.g., emu oil).

As a cleansing component, a combination of anionic and amphoteric surfactants is contained in the present shampoo composition. The anionic surfactants may be selected from a wide variety of alkylsulfates, carboxylates, proteins and amino acids. If the anionic surfactants have $C_{8-22}$ alkyl group or ethylene oxide group thereof, these materials are used as salts with sodium, ammonium, potassium or triethanolamine. The anionic surfactants can be used in amounts from 4% to 30% by weight of the composition, preferably from 8% to 20%. Illustrative of the amphoteric surfactants used, are, for example, betaines (e.g., cocamidopropyl betaine), sultaines (e.g., cocamidopropyl sultaine) and imidazols (e.g., cocoamphocarboxyglycinate). These materials can be used in amount from 1.5% to 10% by weight of the composition, preferably from 2% to 6%. When the combined ratio of anionic surfactants to amphoteric surfactants ranges from 2:1 to 3:1, antiirritating and conditioning effects are expected.

The alkanolamides of fatty acids contained in the present shampoo composition as thickner and/or foamstabilizer include mono or diethanolamide of fatty acids having from 8 to 12 carbon atoms. The preferable examples are lauric diethanolamide, cocamidodiethanolamide, lauroylmiristoyldiethanolamide or cocamidomonoethanolamine, which can be used alone or in mixtures thereof. The preferable amount ranges from 1.5% to 6.0% by weight of the composition.

The polymeric conditioner contained in the present composition may be selected from polyquaternium-10 (Polymer-JR from UCC), guahydroxypropyl-triammonium chloride (Jaguar C-13S from Rhone-Poulenc), polyquaternium-7-(Merquat-550 from Calgon) or mixtures thereof. The preferable amount ranges from 0.12% to 0.55% by weight of the composition.

The non-volatile silicone contained in the present composition as conditioner may be selected from a group consisting of dimethicone, dimethicone copolyol, amodimethicone and mixtures thereof.

The fatty alcohols used in the present composition may be selected from a group consisting of cetyl, stearyl and behenyl alcohols and mixtures thereof. Not only do these materials impart thixotrophy to the shampoo system but also provide gloss to the hair.

To improve consumer acceptability, minor ingredients such as pH regulating agents, humectants, perfumes, dyes and coloring agents can also be added to the present composition. Such conventional ingredients are well known to those skilled in the art.

A pH regulating agent may be added to neutralize the dispersing agent dissolved and thus to ensure the stability of the shampoo system. The useful pH regulating agent includes but is not limited to mono, di and triethanolamine, sodium hydroxide and potassium hydroxide may be examplefied. These materials are used in amounts to render the pH of the composition to be in the range of 5.0 and 7.7.

As suspending and/or pearl agents, glycolstearate may be used in amount from 0.3% to 2.5% by weight of the composition and titanated mica may be used in amount from 0.01 to 0.8% by weight of the composition.

Proteineous hair nutrients and/or physiologically active substances capable of protecting hair or skin, and antioxidants and/or ultraviolet-blocking agents may also be added to the present shampoo composition.

The following examples are given merely as illustrations of the present invention and are not to be considered as limiting. Unless otherwise noted, the percentages therein and throughout the application are by weight.

EXAMPLES 1 to 4

The following shampoo compositions are prepared:

|  | Ingredients | Examples | | | |
|---|---|---|---|---|---|
|  |  | 1 | 2 | 3 | 4 |
| Dispersing Agent-Premix | 1)PVM/MA Decadiene Crosspolymer(5%) | 3.0 | 8.0 | 10.0 | 20.0 |
| Conditioner-Premix | Polyquaternium-10(4%) | — | — | 5.0 | 5.0 |
|  | Cationic Guar Gum(3%) | 10.0 | 5.0 | — | — |
| Cleansing Agent | Ammonium lauryl sulfate(30%) | 20.0 | — | 20.0 | — |
|  | Sodium lauryl ether sulfate(30%) | 25.0 | 25.0 | 25.0 | 25.0 |
|  | Triethanolamine lauryl sulfate(30%) | — | 20.0 | — | 20.0 |
|  | Cocamidopropyl betaine(37%) | 5.0 | 5.0 | — | — |
|  | Cocoamphocarboxy glycinate(48%) | — | — | 4.0 | 4.0 |
| Suspending Agent | Glycol stearate | 1.0 | 1.0 | 0.5 | 0.5 |
| Conditioner | Alkyltrimethylammonium | 1.0 | 1.0 | 0.5 | 0.5 |

-continued

|  | Ingredients | Examples | | | |
|---|---|---|---|---|---|
|  |  | 1 | 2 | 3 | 4 |
|  | chloride(50%) |  |  |  |  |
|  | Cetyl alcohol | 0.5 | 0.5 | 0.25 | 0.25 |
|  | Dimethicone | 0.5 | 1.0 | — | — |
| pH Regulating Agent | Triethanolamine | pH 6.0 | pH 5.5 |  |  |
|  | NaOH(10%) |  |  | pH 6.5 | pH 7.0 |
| Humectant | Propylene glycol | 2.0 | 1.0 | — | — |
|  | Hexylene glycol | — | — | 2.5 | 1.0 |
| Thickner/ | Cocamide DEA | 4.0 | 3.0 | — | — |
| Foamstabilizer | Lauramide DEA | — | — | 2.5 | 3.0 |
| Capsule/Particle | 2)Unisphere | 0.3 | — | — | — |
|  | 3)Nikkol AC | — | 1.0 | — | — |
|  | 4)LipoPearl | — | — | 3.0 | — |
|  | 5)Millisphere | — | — | 1.0 | — |
|  | 6)Millicapsule | — | — | — | 6.0 |
| Hair Nutrients | Hydrolyzed animal protein | 0.3 | 0.3 | 0.3 | 0.3 |
| Additives | Perfume | q.s. | q.s. | q.s. | q.s. |
|  | CaCl$_2$/MgSO$_4$ | — | — | 0.12/ 0.15 | — |
|  | Preservatives | q.s. | q.s. | q.s. | q.s. |
|  | Water | to 100 | to 100 | to 100 | to 100 |

1)PVM/MA Decadiene Crosspolymer: crosslinked copolymer of methyl vinyl ether/maleic anhydride, Stabileze-06 ™ available from ISP, USA.
2)Unisphere: from 0.3 mm to 1.0 mm particles consisting of lactose, cellulose, hydroxymethylcellulose and lipid-soluble vitamin derivatives, available from Induchem, Switzeland.
3)Nikkol AC: capsule with diameter of 0.5–1.5 mm whose wall consists of agar and alginate and in which lipid-soluble vitamins and cushion plant oils such as macadaia oil, meadowfoam oil, jojoba oil and camellia oil are, alone or in combination with the two or more, incorporated, available from Nikko Chemical, Japan.
4)LipoPearl: capsule with diameter of 0.8–5 mm whose wall consisits of animal gelatines and in which animal oils, lipid-soluble vitamins and mineral oils such as liquid paraffin are, alone or in combination with the two or more, incorporated, available from Lipo Technology, USA.
5)Millisphere: sphere having diameter of 0.5–5.0 mm and consisting of alginate, wherein animal and plant oils and lipid-soluble vitamins are incorporated, available from Solabia, France.
6)Millicapsule: capsule with diameter of 1.0–4 mm whose wall consists of polyamides and in which light mineral oils are incorporated, available from Lipotec, USA.

The shampoo compositions are prepared through the following steps:

step 1—PVM/MA decadiene crosspolymer powder is mixed with an appropriate amonut of water in a bath equipped with heater and then the resulting mixture is stirred with increased rate of stirring and by heating to 60° C. or more to produce a homogenous solution (dispersing agent-premix). Separately, polyquaternium-10 and cationic guar gum is dispersed in water at low temperature and subsequently is stirred at high temperature to produce a homogenous solution (conditionerpremix).

step 2—The dispersing agent-premix, conditioner-premix and cleansing agent are poured, while stirring, into a batch in which an appropriate amount of water has been previously contained.

step 3—The suspending agent is added and dissolved by stirring and heating to the temperature of 65° C. or more. After the resulting solution is cooled to the temperature of about 50° C., the conditioners are added therein.

step 4—The humectants and pH regulating agents are together added and stirred to adjust the desired pH of the solution.

step 5—The thickners and foamstabilizers are added and stirred to stabilize the system. At this stage, the temperature of the solution is kept to about 45° C.

step 6—The capsules are added and stirred slowly and gently without any damage. At this stage, if desired, sodium chloride can be incorporated.

step 7—The resulting solution is cooled to the temperature of about 35° C. and then the hair nutrient is added while stirring.

step 8—The preservatives, perfumes and coloring agents are added along with a remaining portion of water and stirred to obtain the desired shampoo composition.

Comparative Examples 1 to 4

As comparision of stability, the following shampoo compositions are prepared:

|  | Ingredients | Comparative Examples | | | |
|---|---|---|---|---|---|
|  |  | 1 | 2 | 3 | 4 |
| Dispersing Agent- Premix | Carbomer(4%) | 35.0 | — | — | — |
|  | Xamthan Gum(3%) | — | 40.0 | — | — |
|  | Carrageenan(3%) | — | — | 40.0 | — |
|  | Hydroxyethyl cellulose(2%) | — | — | — | 15.0 |
|  | Magnesium aluminium silicate(2%) | — | — | — | 20.0 |
| Conditioner- Premix | Polyquaternium-10 (4%) | — | 5.0 | 5.0 | — |
|  | Cationic Guar Gum (3%) | 10.0 | — | — | 10.0 |
| Cleansing Agent | Ammonium lauryl sulfate(30%) | 20.0 | 20.0 | 20.0 | 20.0 |
|  | Sodium lauryl | 25.0 | 25.0 | 25.0 | 25.0 |

-continued

|  | Ingredients | Comparative Examples | | | |
|---|---|---|---|---|---|
|  |  | 1 | 2 | 3 | 4 |
|  | ether sulfate(30%) |  |  |  |  |
|  | Cocamidopropyl betaine(37%) | 5.0 | — | 5.0 | — |
|  | Cocoamphocarboxy glycinate(48%) | — | 4.0 | — | 4.0 |
| Thickner | Cocamide DEA | 3.5 | 3.5 | — | — |
|  | Lauramide DEA | — | — | 3.5 | 3.5 |
|  | Cetyl alcohol | 0.25 | 0.25 | — | 0.25 |
| Capsule | Oil capsule(1–2 mm) | 1.3 | 1.3 | 1.3 | 1.3 |
| Suspending Agent | Glycol stearate | 1.0 | 1.0 | 1.0 | 1.0 |
| pH Regulating Agent | Triethanolamine | — | — | — | pH 7.0 |
|  | NaOH(10%) | pH 7.0 | — | — | — |
| Humectant | Pyrolidone carboxylic acid-Na | 0.5 | — | — | 1.0 |
|  | Propylene glycol | — | 1.5 | 1.5 | — |
| Conditioner | Alkyltrimethylammonium chloride(50%) | 1.0 | 1.0 | 1.0 | 1.0 |
|  | Dimethicone | 0.5 | 0.5. | 0.5 | 0.5 |
|  | Hydrolyzed animal protein | 0.3 | 0.3 | 0.3 | 0.3 |
| Additives | Perfume | q.s. | q.s. | q.s. | q.s. |
|  | Preservatives | q.s. | q.s. | q.s. | q.s. |

-continued

|  | Comparative Examples | | | |
|---|---|---|---|---|
| Ingredients | 1 | 2 | 3 | 4 |
| Citric acid | q.s. | q.s. | q.s. | q.s. |
| Water | q.s. to 100 | q.s. to 100 | q.s. to 100 | q.s. to 100 |

The control shampoo compositions are prepared through a similar procedure as described in Examples 1–4.

The Dispersing agent-Premix and Conditioner-Premix are independently prepared as follows. The carbomer powder (Carbopol-1342 from B. F. Goodrich) is dispersed in water at a high temperature while stirring at a high rate and is dissolved by heating to 60° C. and stirring to produce a homogenous solution. Homogenous solutions of xantham gum or carrageenan can be produced by continuously stirring at a high rate. Homogenous solutions of hydroxyethylcellulose or magnesiumaluminiumsilicate (Veegum HV from R. T. Vanderbilt) can be produced by dispersing the material powders in water while heating to 80° C. and stirring at a high rate and subsequently cooling the resulting dispersion to room temperature. The polyquaternium-(Polymer-JR400 from UCC) or cationic guar gum (Jaguar C-13S from Rhone-Poulenc) are dispersed in water at low temperature and dissolved at a high temperature by stirring to produce the conditioner-premix.

The surfactants (cleansing agents) and water are incorporated together into a batch while slowly stirring. Then, the dispering agent-premix and conditioner-premix are added while heating to 65° C. Subsequently, thickners, suspending agent, humectants, pH regulating agents, encapsulated oily substances, conditioners and other additives are added in appropriate sequences to produce the shampoo compositions.

Stability Test

While each shampoo prepared by the above Examples was stored at 5° C., room temperature(RT) and 45° C. for three months, stability was observed once every two days. In addition, after each shampoo was stored at −10° C. for 24 hours and 45° C. for another 24 hours during a three month period (freeze & thaw test), stability was observed once every two days. The results are shown in Tabel 1 below.

TABLE 1

|  | Examples | | | | Comparative Examples | | | |
|---|---|---|---|---|---|---|---|---|
|  | 1 | 2 | 3 | 4 | 6 | 7 | 8 | 9 |
| 5° C. | stable over 3 months | stable over 3 months | stable over 3 months | stable over 3 months | capsule floated after 6 days | capsule floated after 6 days | stable over 3 months | capsule floated after 4 days |
| RT | stable over 3 months | stable over 3 months | stable over 3 months | stable over 3 months | capsule floated after 6 days | capsule floated after 4 days | stable for 10 weeks | capsule floated after 6 days |
| 45° C. | stable over 3 months | stable over 3 months | stable over 3 months | stable over 3 months | capsule floated after 2 days | capsule floated after 6 days | stable for 10 weeks | capsule floated after 2 days |
| F & T | stable for 6 weeks | stable for 2 months | stable for 2 months | stable over 3 months | capsule floated after 1 cycle | capsule floated after 1 cycle | stable for 5 weeks | capsule floated after 1 cycle | the above results, it is demonstrated that the shampoo compositions according to the present invention have remarkably superior stability. In contrast, the comparative shampoo compositions are less stable since the phases of the capsules containing oily substances are formed within a week. Although the shampoo composition of Comparative Example 3 shows relatively good stability, it is less stable than the present shampoo composition and it would have an adverse effect on the hair since it contains carrageenan.

Comparative Examples 5–9

To compare performace, the plain shampoo compositions (Comparative Examples 5 and 6) and the conditioning shampoo compositions (Comparative Examples 7, 8 and 9) are prepared:

|  | Comparative Examples | | | | |
| --- | --- | --- | --- | --- | --- |
|  | 1 | 2 | 3 | 4 | 5 |
| Sodium lauryl sulfate (30%) | 15.0 | — | — | — | — |
| Sodium lauryl ether sulfate(30%) | 25.0 | — | 25.0 | 25.0 | 25.0 |
| Ammonium lauryl sulfate(30%) | — | 20.0 | 20.0 | 20.0 | 25.0 |
| Ammonium lauryl ether sulfate(30%) | — | 25.0 | — | — | — |
| Triethanolamine lauryl sulfate(30%) | 5.0 | — | — | — | — |
| Cocamidopropyl betaine(37%) | 5.0 | — | 5.0 | 4.0 | — |
| Cocoamphocarboxy-glycinate(48%) | — | 4.0 | — | 4.0 | — |
| Cocamide DEA | 3.5 | 3.5 | 3.0 | 3.5 | 3.5 |
| Cationic Guar Gum | — | — | — | — | 0.3 |
| Polyquaternium-10 | 0.3 | 0.3 | — | — | — |
| Carbomer | — | — | — | 0.5 | 0.25 |
| Triethanolamine | — | — | — | — | — |
| Xanthan Gum | — | — | 0.35 | | |
| Glycol Stearate | — | 1.0 | 1.0 | 1.0 | 1.0 |
| Propylene Glycol | 1.5 | 1.5 | 1.0 | 1.0 | 1.0 |
| Hydrolyzed Animal Protein | 0.3 | 0.3 | 0.4 | 0.4 | 0.4 |
| Cetyl Alcohol | — | — | 0.2 | 0.2 | 0.2 |
| Dimethicone | — | — | 1.0 | 1.0 | 1.0 |
| alkyltrimethylammonium chloride(50%) | — | — | — | 1.0 | 1.0 |
| Preservatives | q.s. | q.s. | q.s. | q.s. | q.s. |
| Perfume | q.s. | q.s. | q.s. | q.s. | q.s. |
| Citric Acid | q.s. | q.s. | q.s. | q.s. | q.s. |
| Coloring Agent | q.s. | q.s. | q.s. | q.s. | q.s. |
| Water | to 100 | to 100 | to 100 | to 100 | to 100 |

The comparative shampoo compositions are prepared as described in Examples 1 through 4.

Performance Test

After each sample of shampoo compositions, as prepared in Examples 1–4 and Comparative Examples 5–9, was applied for 3 weeks, 2 to 5 times each week to twenty five(25) women who were between the ages of 18 to 40, testing was conducted regarding foamability, feeling for shampoo, rinse ability, combability after briefly drying the hair, conditioning of the hair after it was dried, elasticity and volume-up of the hair after it was dried. Each performance was tested on a seven degrading scale (seven being the highest score) and the results of the test are shown in Table 2 below. The marks were obtained by averaging results of the 25 women.

TABLE 2

|  | Examples | | | | Comparative Examples | | | | |
| --- | --- | --- | --- | --- | --- | --- | --- | --- | --- |
|  | 1 | 2 | 3 | 4 | 5 | 6 | 7 | 8 | 9 |
| Foamability | 4.0 | 4.2 | 4.2 | 4.3 | 4.5 | 3.9 | 3.8 | 3.4 | 3.5 |
| Feeling | 4.5 | 5.7 | 5.8 | 5.8 | 3.4 | 3.2 | 3.8 | 3.9 | 4.1 |
| Linse ability | 4.7 | 5.4 | 5.3 | 5.4 | 2.8 | 3.6 | 4.3 | 4.0 | 4.3 |
| Combability | 4.3 | 4.8 | 5.5 | 5.3 | 3.2 | 3.3 | 3.1 | 4.1 | 4.0 |
| Conditioning | 4.9 | 5.5 | 5.9 | 5.9 | 3.4 | 3.4 | 3.6 | 3.7 | 4.1 |
| Elasticity & Volume-up | 5.0 | 5.4 | 5.6 | 6.0 | 3.2 | 3.1 | 3.5 | 3.3 | 3.3 |

The above results show that the shampoo compositions of Examples 1 through 4 keep capsules containing oily substances stably and homogeneously dispersed and therefore have excellent performance by successfully applying oily substances encapsulated to the hair.

What is claimed is:

1. A shampoo composition comprising (a) from 0.05% to 10% by weight of capsules or particles of 0.2 to 6.0 mm in diameter which include oily substances, (b) from 5% to 65% by weight of surfactants selected from the group consisting of anionic surfactants, amphoteric surfactants and mixtures thereof, (c) from 0.15% to 2% by weight of copolymer of methyl vinyl ether/maleic anhydride decadiene crosspolymer and (d) from 0.1% to 2.0% by weight of polymeric conditioners.

2. The shampoo composition according to claim 1 wherein the capsules or particles are contained in amount from 0.15% to 6.0% by weight and the copolymer of methyl vinyl ether/maleic anhydride decadiene crosspolymer are contained in amount from 0.2% to 1.3% by weight.

3. The shampoo composition according to claim 1 containing from 0.5% to 10% by weight of alkanolamide of fatty acid, from 0.1% to 4% by weight of salt of alkylmethylammonium and from 0.15% to 2% by weight of nonvolatile silicone or fatty alcohol.

4. The composition according to claim 3, containing diethanolamine, triethanolamine, sodium hydroxide or potassium hydroxide.

5. The composition according to claim 3 wherein the alkanolamide of fatty acid is selected from the group consisting of mono and dialkanolamide of fatty acids having from 8 to 14 carbon atoms and mixtures thereof.

6. The composition according to claim 3 wherein the salt of alkylmethylammonium is selected from the group consisting of alkyltrimethylammonium chloride, dialkyldimethylammonium chloride, tricetylmethylammonium chloride and mixtures thereof and has from 10 to 24 carbons.

7. The composition according to claim 3, containing dimethicone, amodimethicone, dimethicone copolyol or mixtures thereof.

8. The composition according to claim 3 wherein the fatty alcohol has from 10 to 24 carbons.

9. The shampoo composition according to claim 2 containing from 0.5% to 10% by weight of alkanolamide of fatty acid, from 0.1% to 4% by weight of salt of alkylmethylammonium and from 0.15% to 2% by weight of nonvolatile silicone or fatty alcohol.

10. The composition according to claim 9, containing diethanolamine, triethanolamine, sodium hydroxide or potassium hydroxide.

11. The composition according to claim 9 wherein the alkanolamide of fatty acid is selected from the group consisting of mono and dialkanolamide of fatty acids having from 8 to 14 carbon atoms and mixtures thereof.

12. The composition according to claims 9 wherein the salt of alkylmethylammonium is selected from the group consisting of alkyltrimethylammonium chloride, dialkyldimethylammonium chloride, tricetylmethylammonium chloride and mixtures thereof and has from 10 to 24 carbons.

13. The composition according to claim 9, containing dimethicone, amodimethicone, dimethicone copolyol or mixtures thereof.

14. The composition according to claim 9 wherein the fatty alcohol has from 10 to 24 carbons.

15. The composition according to claim 1 wherein the oily substance incorporated in said capsule or particle is selected from the group consisting of liquid paraffin and derivatives thereof, vitamin A and E and derivatives, meadowfoam oil, jojoba oil, macadamia nut oil, cushion oil, emu oil, and mixtures thereof.

16. The composition according to claim 1 wherein the capsule has a wall made of any component selected from the group consisting of agar, alginate, gelatine, polyamide, lactose, cellulose and derivatives thereof, and mixtures thereof.

17. The composition according to claim 1 wherein the capsule has a wall of a thickness ranging from 50 µm to 500 µm.

18. The composition according to claim 1 wherein the diameter of the capsule is from 0.3 mm to 3.0 mm.

19. The composition according to claim 1 wherein the composition has a pH ranging from 5.0 to 7.7.

20. The composition according to claim 2 wherein the oily substance incorporated in said capsule or particle is selected from the group consisting of liquid paraffin and derivatives thereof, vitamin A and E and derivatives, meadowfoam oil, jojoba oil, macadamia nut oil, cushion oil, emu oil, and mixtures thereof.

21. The composition according to claim 2 wherein the capsule has a wall made of any component of the group consisting of agar, alginate, gelatine, polyamide, lactose, cellulose and derivatives thereof, and mixtures thereof.

22. The composition according to claim 2 wherein the capsule has a wall of a thickness ranging from 50 µm to 500 µm.

23. The composition according to claim 2 wherein the diameter of the capsule is from 0.3 mm to 3.0 mm.

24. The composition according to claim 2 wherein the composition has a pH ranging from 5.0 to 7.7.

* * * * *